(12) United States Patent
Miller (10) Patent No.: US 8,319,953 B2
(45) Date of Patent: Nov. 27, 2012

(54) METHOD AND DEVICE FOR SPECTRALLY DETECTING PRESENCE OF BLOOD

(75) Inventor: David Miller, Morgan, UT (US)

(73) Assignee: Spectra Tracker LLC, Layton, UT (US)

( * ) Notice: Subject to any disclaimer, the term of this patent is extended or adjusted under 35 U.S.C. 154(b) by 196 days.

(21) Appl. No.: 12/721,354

(22) Filed: Mar. 10, 2010

(65) Prior Publication Data

US 2010/0231893 A1     Sep. 16, 2010

Related U.S. Application Data

(60) Provisional application No. 61/158,790, filed on Mar. 10, 2009.

(51) Int. Cl.
*G01N 33/48* (2006.01)
(52) U.S. Cl. .......................................... 356/39
(58) Field of Classification Search .................... 356/39, 356/40; 600/371
See application file for complete search history.

(56) References Cited

U.S. PATENT DOCUMENTS

| 4,655,225 | A | | 4/1987 | Dähne et al. | |
|---|---|---|---|---|---|
| 4,796,636 | A | * | 1/1989 | Branstetter et al. | 600/330 |
| 4,805,623 | A | | 2/1989 | Jöbsis | |
| 5,059,394 | A | * | 10/1991 | Phillips et al. | 422/68.1 |
| 5,363,152 | A | | 11/1994 | Reed, III | |
| 5,729,333 | A | | 3/1998 | Osten et al. | |
| 5,734,464 | A | * | 3/1998 | Gibbs | 356/39 |
| 5,830,133 | A | | 11/1998 | Osten et al. | |
| 5,898,487 | A | | 4/1999 | Hage | |
| 5,936,714 | A | * | 8/1999 | Gibbs | 356/39 |
| 6,749,565 | B2 | | 6/2004 | Chudner | |
| 6,791,674 | B2 | | 9/2004 | Kawano | |
| 7,009,180 | B2 | | 3/2006 | Sterling et al. | |
| 7,290,896 | B2 | | 11/2007 | Dallas et al. | |
| 7,545,487 | B2 | * | 6/2009 | Kok et al. | 356/53 |
| 7,749,217 | B2 | * | 7/2010 | Podhajsky | 606/34 |
| 2002/0019587 | A1 | | 2/2002 | Cheng et al. | |
| 2004/0179362 | A1 | | 9/2004 | Klatt | |
| 2004/0223342 | A1 | | 11/2004 | Klipstein et al. | |
| 2006/0044792 | A1 | | 3/2006 | Dallas et al. | |

* cited by examiner

*Primary Examiner* — Roy M Punnoose
(74) *Attorney, Agent, or Firm* — John R. Thompson; Stoel Rives LLP (57) ABSTRACT

The present disclosure provides systems and methods for detecting the presence of blood. Specific applications may include hunting, during which it may be necessary to track a wounded, bleeding animal. According to one embodiment, a device transmits light at one or more wavelengths to irradiate a region potentially containing blood. Hemoglobin in the blood absorbs or reflects more of the transmitted light than other matter in the region. A detector detects the light reflected from the region and determines if blood is present in the region using spectral analysis.

25 Claims, 8 Drawing Sheets

FIG. 8

METHOD AND DEVICE FOR SPECTRALLY DETECTING PRESENCE OF BLOOD

RELATED APPLICATIONS

The present application claims the benefit under 35 U.S.C. §119(e) of U.S. Provisional Patent Application No. 61/158,790 filed Mar. 10, 2009, titled "Method and Device for Spectrally Detecting the Presence of Blood," which application is incorporated herein by reference in its entirety.

TECHNICAL FIELD

This disclosure generally relates to systems and methods for the detection of blood. More particularly, the present disclosure may be utilized in any field in which it is desirable to detect the presence of blood, including but not limited to hunting, forensic sciences, military applications, and the like.

BRIEF DESCRIPTION OF THE DRAWINGS

Additional aspects and advantages will be apparent from the following detailed description of preferred embodiments, which proceeds with reference to the accompanying drawings.

In the following description, numerous specific details are provided for a thorough understanding of the various embodiments disclosed herein. However, those skilled in the art will recognize that the systems and methods disclosed herein can be practiced without one or more of the specific details, or with other methods, components, materials, etc. In addition, in some cases, well-known structures, materials, or operations may not be shown or described in detail in order to avoid obscuring aspects of the disclosure. Furthermore, the described features, structures, or characteristics may be combined in any suitable manner in one or more alternative embodiments.

DETAILED DESCRIPTION

There are many instances in which it is desirable to detect blood. Blood, both dry and wet, contains a significant amount of hemoglobin. Hemoglobin absorbs and reflects light at varying amounts based on the wavelength of light. For example, hemoglobin reflects more light around 700 nanometers (nm) and absorbs more light around 400 nm. Disclosed herein are systems and methods for examining a region to detect the presence of blood using spectral analysis of reflected light.

One possible application for the systems and methods disclosed herein involves tracking blood left by a wounded animal during hunting. Hunting big game animals, such as elk and deer, may require tracking a wounded animal using a blood trail. This is especially true in bow hunting where the strike force of the arrow may not be sufficient to instantly kill the animal. Rather, the wound inflicted by an arrow may cause sufficient blood loss to kill an animal over a period of time. If the animal flees while bleeding, it may be necessary to track the animal for a considerable distance until it succumbs to the blood loss.

The nature of some hunting wounds coupled, with the physiology of the animal and the animal's environment, may result in an intermittent blood trail. That is, the animal may bleed profusely at times and nearly cease to bleed at others. During times of low bleeding, the blood trail may become difficult for a hunter to follow, as only a few drops of blood may be present. Adding to the difficulty, hunting often occurs in autumn when many colored leaves are present. Additional problems of visually detecting blood drops arise in low light conditions, such as heavily wooded forests or after sunset.

According to one embodiment, an area is illuminated with light at two or more wavelengths. One of the selected wavelengths may be generally absorbed by hemoglobin. The second wavelength of light may be used in various embodiments as a control wavelength to establish a baseline reflection intensity. Light at both wavelengths is reflected from the area under examination and collected by a receiver. A spectral analysis of the intensities of the light at the two wavelengths may be used to determine if blood is present in the area.

In certain embodiments, the second wavelength of light is a wavelength of light generally absorbed by hemoglobin. Alternative embodiments may include any number of wavelengths of light absorbed and/or reflected by hemoglobin and/or other substances present in the region under examination. For example, a device configured for use by a hunter may utilize light having at least one wavelength strongly reflected and/or absorbed by leaves and other objects found in the outdoors to establish a baseline control signal and at least one other wavelength strongly absorbed by hemoglobin. In another example, a device configured for indoor forensic analysis may utilize light having at least one wavelength strongly reflected and/or absorbed by items typically found indoors, such as carpet, upholstery, and the like to establish a baseline control signal and at least one other wavelength generally absorbed by hemoglobin.

A blood detection device may include a light transmitter and light detector. The device may be handheld and/or portable. One embodiment may include a telescoping handle to provide a compact storage size and yet allow an operator to extend a transmitter and receiver during use. Additionally, it may be possible to adjust the beam width of the light emitted from a transmitter and/or adjust the size of the area from which a receiver collects light.

Generally, wavelengths of light less than approximately 600 nm are absorbed by hemoglobin more than wavelengths between about 600 nm and 1,000 nm. According to various embodiments, the wavelengths of light used for detection are based on substances that are likely present in a region under examination. For example, in hunting applications, substances such as dirt, leaves, wood, and the like, may be expected in an area under examination. Each of these substances may absorb and reflect light differently based on wavelength. Various embodiments may also be configured to overcome ambiguities in absorption and/or reflection patterns by using specific wavelengths of light or a larger number of wavelengths. For example, it may be desirable to select specific wavelengths of light that are strongly absorbed by blood and strongly reflected by other substances in the region.

Certain embodiments may include multimode detection that may enhance the probability of blood detection. One such multimode approach may include combining the response of a selective wavelength photo-spectroscopy system with visual inspection. In still other embodiments, natural light is used as a broad-spectrum illuminating source. According to such embodiments, optical filters may be used to detect wavelengths of interest.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. In particular, an "embodiment" may be a system, a method, or a product of a process.

In the following description, numerous details are provided to give a thorough understanding of various embodiments. One skilled in the relevant art will recognize, however, that the embodiments disclosed herein can be practiced without one or more of the specific details, or with other methods, components, materials, etc. In other instances, well-known structures, materials, or operations are not shown or described in detail to avoid obscuring aspects of this disclosure.

Additionally, throughout the specification light and wavelengths of light refer to various frequencies of electromagnetic radiation. Thus, the term light, as used herein, is not intended to be restricted to visible light, but rather to extend into what are typically referred to as the infrared and ultraviolet ranges. Furthermore, systems and methods described as emitting or detecting a particular wavelength of light may in practice emit or detect a range of wavelengths within a band including the particularly described wavelength.

As illustrated and described below, according to various embodiments, the present systems and methods rely on the absorption of light at specific wavelengths by hemoglobin. Accordingly, the unique spectral signature of hemoglobin, which is described below, may be used to recognize when blood is present in a region. Specific embodiments and examples are described below in conjunction with the drawings.

Figure 1:
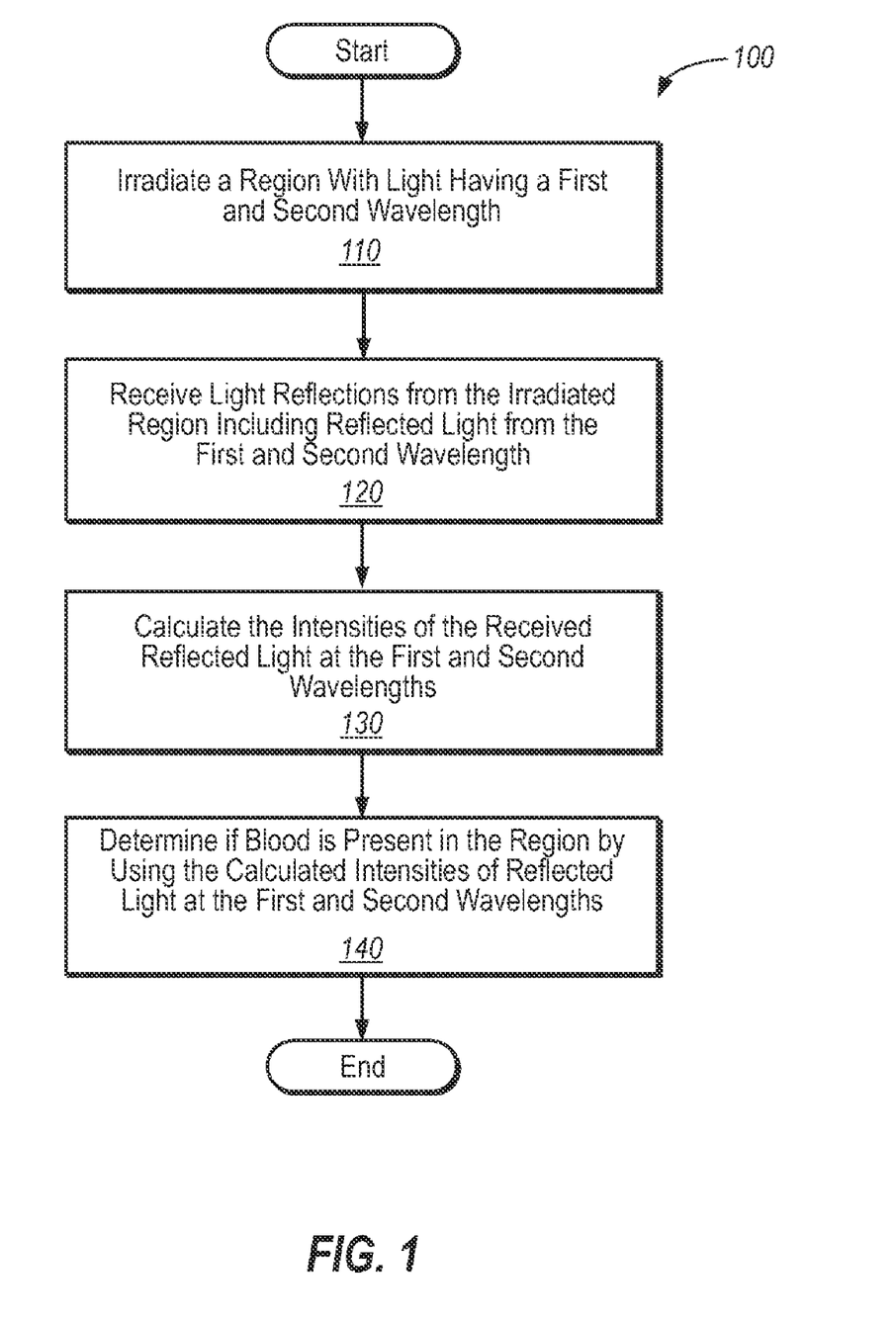
FIG. 1 illustrates a flow diagram of an exemplary method to determine if blood is present in a region using spectral analysis of reflected light.

FIG. 1 illustrates an exemplary method 100 of determining if blood is present in a region by comparing the intensities of light at specific wavelengths reflected by a region under examination. According to one embodiment, at 110, a region is irradiated with light having a first and second wavelength. The first wavelength may correspond to a wavelength that is strongly absorbed by hemoglobin. Thus, if blood is present in the region, less of the first wavelength of light may be reflected than would be reflected if blood were not present in the region. Further, light at the second wavelength may correspond to a wavelength that is strongly reflected by substances in the region and thus may be used as a baseline or control wavelength.

After irradiating a region with light having at least two wavelengths, reflected light from the region may be received at 120. According to one embodiment, only light at specific wavelengths is detected. The detection of the intensity of specific wavelengths may be performed using any number of detection devices, including photodiodes, charge-coupled devices (CCDs), complementary metal-oxide-semiconductor (CMOS) active pixel sensors (APSs), spectrometers, and the like. Additionally, optical filters may be used to isolate and detect specific wavelengths. Additional details regarding detection methods and systems are provided below. Regardless of the light detection system used, the relative intensities of the received light reflections at the first and second wavelengths may be calculated at 130. At 140, it is determined if blood is present in the irradiated region using the calculated intensities of the received light reflections at the first and second wavelengths.

In one example, a light source outputs light at 700 nm and 425 nm. Hemoglobin in blood strongly absorbs light at 425 nm and strongly reflects light at 700 nm. Other substances in the region may not strongly reflect or strongly absorb light at either 700 nm or 425 nm. If a region without blood is examined, light from both wavelengths may be expected to reflect off the region at approximately the same intensity. However, if blood is present in the region, the intensity of the light reflected at 700 nm may be greater than the intensity of light reflected at 425 nm, as the light at 425 nm is more strongly absorbed by the hemoglobin in the blood.

Figure 2:
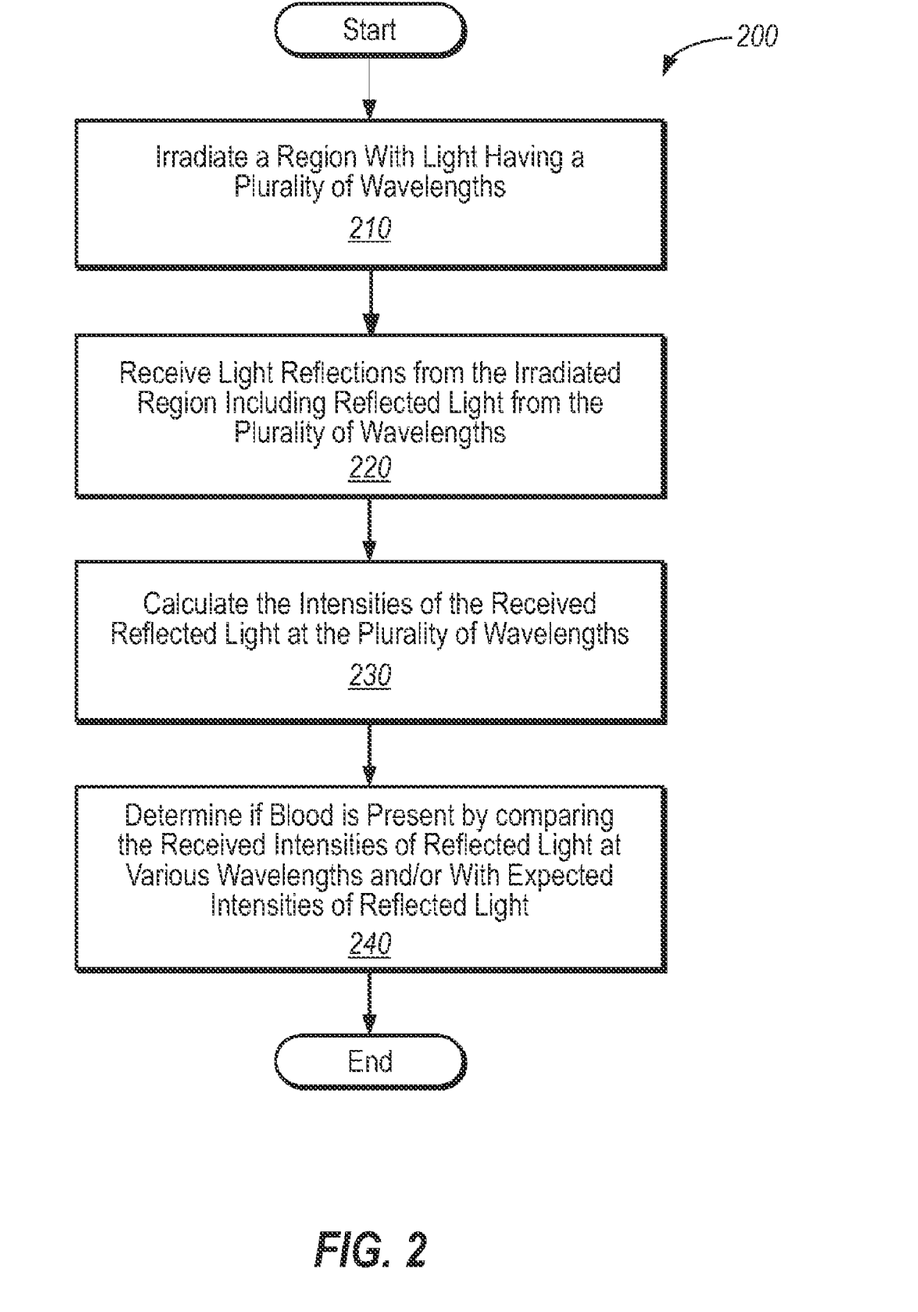
FIG. 2 illustrates a flow diagram of an exemplary method to determine if blood is present in a region using spectral analysis of reflected light at multiple wavelengths.

FIG. 2 illustrates one embodiment of a method 200 of determining if blood is present in a region using a plurality of wavelengths to distinguish between blood and other substances present, or potentially present, in the region. The region is irradiated with light having a plurality of wavelengths at 210. In various embodiments, the irradiated region may be irradiated by light from the sun. At 220, light reflected from the irradiated region is received, including light reflected at each of the plurality of wavelengths. The intensities of each of the plurality of wavelengths received are calculated at 230. At 240, it may be determined if blood is present in the region by comparing the intensities of the received reflected light at each of the various wavelengths with one another and/or with expected intensities of reflected light.

Various embodiments may use a plurality of wavelengths to resolve ambiguities as to whether blood is present in a region. Such embodiments may be described as multi-mode detectors. For example, hemoglobin in blood strongly reflects light in the 600 nm to 1,000 nm range while strongly absorbing light in the 350 nm to 600 nm range. Other substances in the region may absorb and reflect various wavelengths of light at various intensities; however, it is unlikely that other substances will absorb and reflect light in a pattern similar to that of hemoglobin. The intensities with which hemoglobin absorbs and reflects light at various wavelengths can be described as an absorption signature. It is unlikely that other substances in the region will have identical or similar absorption signatures to that of hemoglobin. Thus, a plurality of wavelengths may be utilized to increase the accuracy of the determination of whether blood is present in the region.

Figure 3:
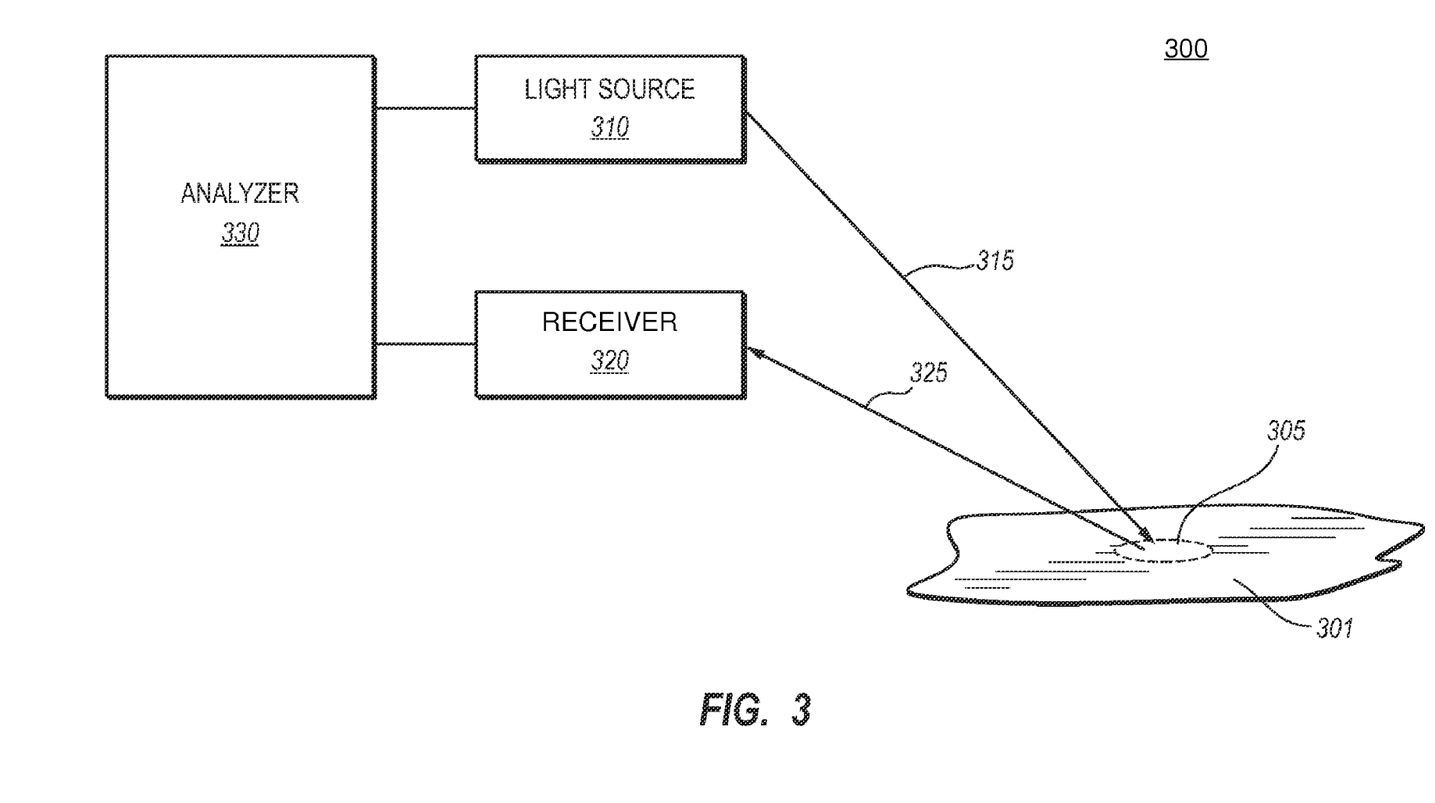
FIG. 3 illustrates an exemplary block diagram of a blood detection system configured to detect the presence of blood.

FIG. 3 illustrates an exemplary block diagram of a system 300 configured to detect blood in a region 301. A light source 310 is used to generate a beam of light 315. The beam of light 315 is focused on a specific region 301 containing a small amount of blood 305. According to various embodiments, the beam of light 315 comprises light at one or more specific wavelengths. The light source 310 may comprise one or more light emitting diodes and/or laser diodes configured to emit light at one or more specific wavelengths or ranges of wavelengths. According to various alternative embodiments, the light source 310 may comprise any of a number of light sources capable of emitting a broad spectrum of light. In such embodiments, filters may be utilized to identify specific wavelengths or ranges of wavelengths in light reflected from the region 301. According to one embodiment, the light source 310 may comprise one or more coherent light sources, such as a laser, laser diode, or similar device. According to such an embodiment, a coherent light source and corresponding detector may be used to distinguish light emitted from the light source 310 and ambient light.

According to one embodiment, at least one wavelength emitted from the light source 310 is strongly absorbed by hemoglobin. The light source 310 may also emit light at a second wavelength that is used to calibrate an analyzer 330 and establish a baseline intensity of reflected light. The second wavelength may be referred to as a control signal.

A receiver 320 may be positioned to receive reflected light 325 from the region 301. The receiver 320 may be configured to calculate the intensity of light at one or more wavelengths. According to various embodiments, as described in more detail below, the receiver 320 may utilize one or more optical filters coupled with photodiodes that are sensitive to a relatively wide bandwidth of light. Alternatively, the receiver 320 may comprise one or more photodiodes configured to detect a narrow range of wavelengths or a single wavelength. According to one embodiment, the receiver 320 may comprise a CCD, CMOS APS, spectrometer, and/or other device capable of detecting the intensity of light at one or more wavelengths. The analyzer 330 compares the intensities of light at specific wavelengths received by the receiver 320 to determine if blood 305 is present in the region 301. In certain embodiments, the lack of light, or diminished intensity of light, at a particular wavelength may be used to determine if blood 305 is present in the region 301.

Figure 4:
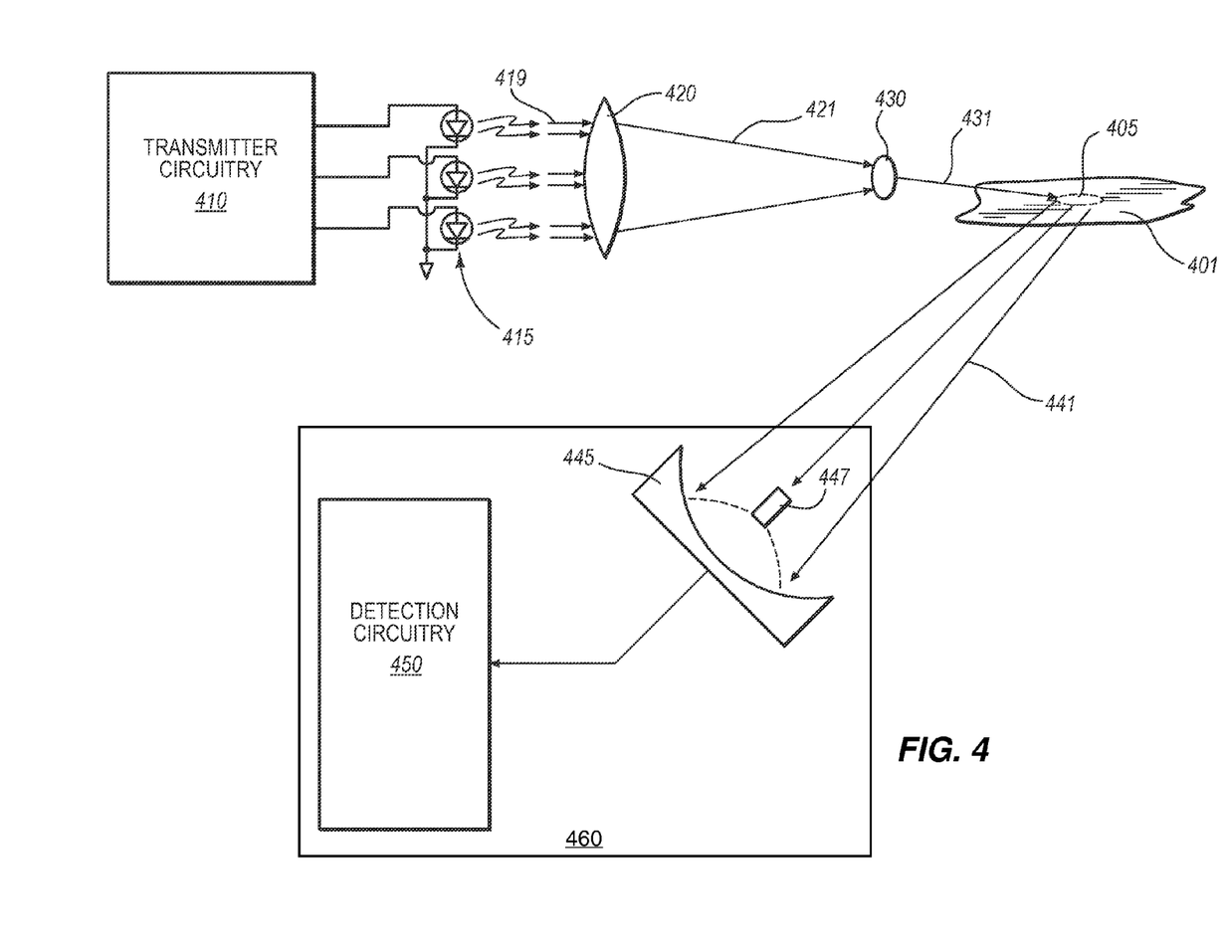
FIG. 4 illustrates a block diagram of one exemplary configuration of a transmitter and detector configuration for use in a blood detection system.

FIG. 4 illustrates one exemplary embodiment of a light source 415 and a receiver 460. As illustrated in FIG. 4, the light source 415 is controlled by transmitter circuitry 410. In the illustrated embodiment, transmitter circuitry 410 is configured to selectively control the light emitting diodes (LEDs) that comprise the light source 415. Light 419 generated by the light source 415 is focused by a lens 420, and optionally passes through a filter 430 before irradiating a region 401, which may or may not include blood 405. The lens 420 may be configured to provide a divergence angle of the light beam 421 that is as wide as possible, without overly reducing the signal-to-noise ratio of the light reflected 441 from the region 401. The wider the divergence or beam width, the larger the region that can be scanned with each sweep of the light beam 421; however, the larger the beam width, the smaller the ratio of illuminated blood to substances other than blood, and thus the weaker the signal (e.g., blood response) to noise (e.g., substances other than blood) ratio becomes. Larger beam widths may reduce the probability of blood detection, while smaller beam widths may require additional time to examine a particular region. Therefore, the desired beam divergence is generally constrained by the signal to noise ratio and the speed with which a region is examined. In one embodiment configured for use in hunting applications, a beam divergence of approximately ten degrees may yield an acceptable result. Other applications or situations may require a different beam divergence to maximize performance.

According to one embodiment, the light beam 421 may pass through one or more filters 430 to filter some wavelengths of light, thus causing only specific wavelengths of light to irradiate the region 401. Such filters 430 may be placed before or after the lens 420. The light 441 reflected from the region 401, and potentially the blood 405, is received by a photodiode 447, or similar device. According to the illustrated embodiment, a parabolic reflector 445 collects the reflected light 441 and focuses it onto a detector 447.

By way of example, the detector 447 may be a broad-spectrum photodiode. Alternatively, the detector may be configured to detect a narrow bandwidth of light. According to various embodiments, a selective fixed wavelength photodiode or a voltage controlled selective wavelength photodiode is used. According to alternative embodiments, multiple selective wavelength photodiodes (fixed or voltage controlled) are used to detect the intensities of reflected light at various wavelengths. According to yet another embodiment, broad-spectrum photodiodes are used in conjunction with optical filters to determine the intensities of light at specific wavelengths.

According to one embodiment, the region 401 may be irradiated with broad-spectrum light, such as the light source 415 or alternatively natural sunlight, and the detector 447 may be a detection element capable of measuring the intensity of light at various wavelengths. By subtracting out a measurement of ambient light, the system is able to spectrally analyze only the transmitted light reflected from the region. Such embodiments may, therefore, be relatively immune to sunlight saturation. A decrease in light intensity of wavelengths absorbed by hemoglobin may indicate that blood 405 is present in the region 401.

Transmitter circuitry 410 may utilize amplitude modulation in various embodiments to allow the detection circuitry 450 to differentiate between ambient light and the transmitted light 431. The spectral signature received by the detector 447 may then be processed to extract discrete wavelength information. Also, statistical-based processing techniques, such as multi-variant analysis (curve fitting), may be applied to continuous spectral signatures to detect the presence of blood.

According to one embodiment, the transmitted light 431 cycles through a predetermined number of wavelengths and the detector 447 detects the intensity of each wavelength as it is reflected off the region 401. For example, the transmitted light 431 may include only one specific wavelength at a given time. In a given period of time, each LED may be used to illuminate the region 401. In the illustrated embodiment, the light source 415 includes three LEDs, however, in other embodiments the light source 415 may include any number of LEDs, each of which may produce a specific wavelength. The detector 447, coupled with the detection circuitry 450, may then be able to determine the intensity of reflected light for each of the reflected wavelengths.

Detection circuitry 450 may be configured to compensate for the distance between the lens 430 and the region 401. In various embodiments, the detection circuitry 450 may be configured to account for the varying reflectivity of different surfaces located in the region 401.

Three or more wavelengths of light may be utilized in certain embodiments. Light at a first wavelength may be strongly absorbed by hemoglobin, while light at a second wavelength may be strongly reflected by hemoglobin. The second wavelength may be used to identify the specific spectral signature of hemoglobin. The third wavelength may be utilized to account for substances other than blood that are likely to be found in the region 401 (e.g., dirt, leaves, etc., in embodiments used for hunting). In some instances it may be desirable to use three or more different wavelengths to obtain a desirable signal-to-noise ratio and to increase the statistical accuracy of the device.

Various embodiments of systems according to the present disclosure can be used to detect both hydrated (e.g., fresh) and dry blood. The primary difference between hydrated and dry blood is the content of water. Although the visible color of dried blood may differ from fresh blood, the amount of hemoglobin present does not. In one embodiment, wavelengths of light are selected that are not significantly affected by the presence of water. For example, water is nearly transparent to light from the ultraviolet region through most of the visible light region, and accordingly, light in these regions may be utilized to detect both fresh and dry blood.

When the area examined is large, and particularly the area examined is outside, many competing or erroneous light sources are present, such as ambient light, stray reflections, and the like. Various approaches may be used to remove unwanted light from calculations, such as modulation of the illuminating light source, digital signal processing, optical and electrical filtration, and the like.

In some embodiments, a feedback mechanism, such as an LED indicator, vibrator, audible tone, prerecorded audio messages, flashing lights, or the like, is used to indicate when blood is detected. According to one embodiment, a user may select the feedback mechanism from a list of available feedback mechanisms. This may allow a user to disable audible tones that may also alert nearby animals.

As will be appreciated, when tracking animals that are leaving a blood trail due to a mortal wound, the trail may extend for a considerable distance. Plotting such a trail may give an indication to the hunter where the animal is headed. In accordance with one embodiment, a blood detection device is capable of receiving position information from the Global Position System (GPS). According to one embodiment, each time a blood drop is detected, a marker or waypoint may be plotted using the location information from the GPS device to establish a blood trail. In one embodiment, a GPS is built directly into a blood detection device. In other embodiments, a GPS is coupled to an appropriate electronic interface. One embodiment may include a display capable of plotting the course of the animal. Certain embodiments may also project the direction of an animal based on the detected blood spots and the terrain.

According to various embodiments, a blood detection system is capable of accommodating signal strength variations of many orders of magnitude. In some embodiments, logarithmic amplification, automatic gain control (AGC), and the like are used to keep the instrument from either saturating or losing a signal.

A blood detection device may be housed in various configurations. For example, the device may be housed in a flashlight-type body with optical components located in the head of the light and electronics in the body. In a typical flashlight arrangement, the device may be held somewhere between waist and chest height as the beam is directed toward points of interest. For an average person, this means that the head of the device will be located 36 to 48 inches above the ground. In one embodiment, the device is provided with a telescoping handle that allows the head to extend out, thus allowing the detection components to be placed closer to the ground. This may increase the resolving power of the device. An exemplary embodiment including a telescoping handle is described in detail below.

Figure 5:
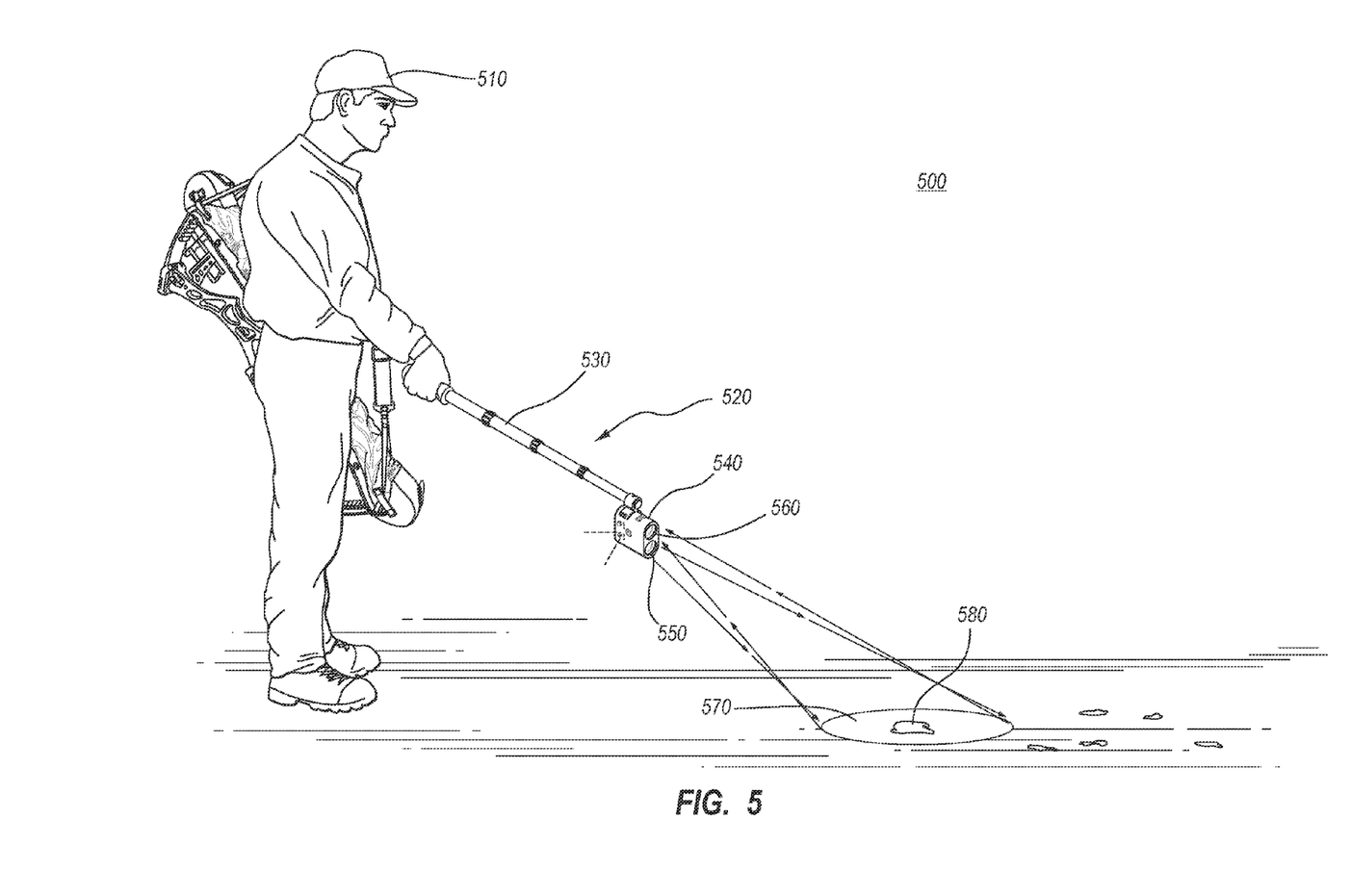
FIG. 5 illustrates one embodiment of an exemplary blood detection system in use.

FIG. 5 illustrates an exemplary blood detection device 520 in use 500. As illustrated, a bow hunter 510 is tracking a blood trail including a blood spot 580 with the blood detection device 520. The blood detection device 520 comprises a telescoping handle 530, and a head portion 540. As illustrated, the blood detection device 520 is in an extended position; that is, the telescoping handle 530 is fully extended. According to various embodiments, a power source, such as batteries or solar cells, for the blood detection device 520 is located in the handle 530 or the head portion 540 of the blood detection device 520. According to various embodiments, analysis and processing of received signals is performed internally in the head portion 540. The head portion 540 may comprise a transmitter 550 and a receiver 560. As illustrated, the transmitter 550 irradiates the region 570 with light at one or more wavelengths, while the receiver 560 receives the reflected light for spectral analysis to determine if blood is present in the region 570.

According to one embodiment, transmitted light at a first wavelength is strongly absorbed by the blood spot 580 and reflected by the remaining materials in the region 570. According to this embodiment, transmitted light at a second wavelength is generally reflected by both the blood spot 580 and by other substances in region 570. Thus, the receiver 560 will detect a greater intensity of light at the second wavelength than at the first wavelength. Upon analysis, the device 540 may compare the received reflected intensities and determine that blood is present, since some of the light at the first wavelength was absorbed by the blood 580. As previously described, to improve accuracy or account for various potential substances in the region 570, the blood detection device 520 may transmit, receive, and/or analyze any number of wavelengths or ranges of wavelengths of light.

Although FIG. 5 illustrates an embodiment specifically configured for following an animal's blood trail on a hunt, it will be readily apparent to the skilled artisan that similar principles may be applied to other applications, such as military applications, forensic science, and other uses.

Figure 6:
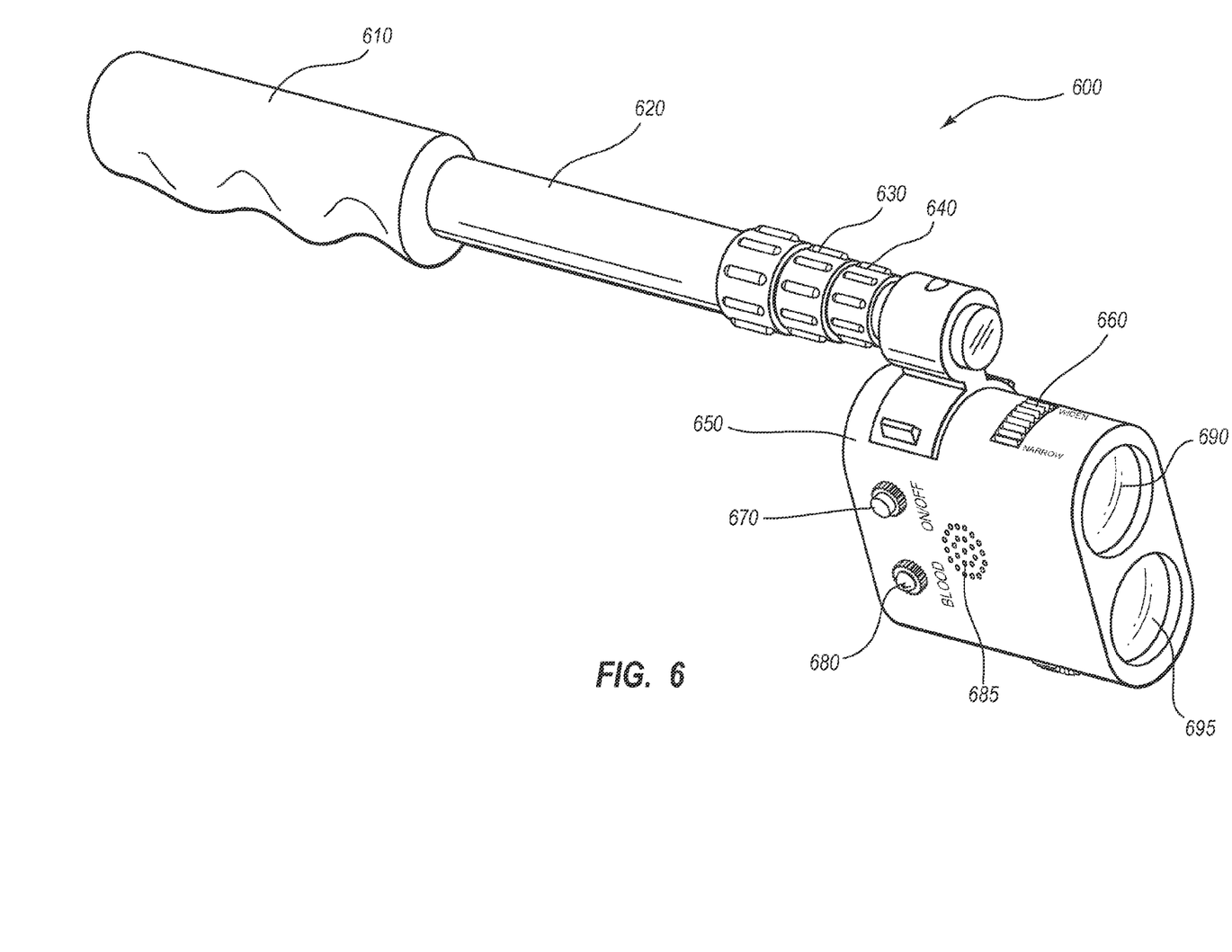
FIG. 6 illustrates one embodiment of an exemplary blood detection system that includes a telescoping handle.

FIG. 6 illustrates a closer view of one exemplary blood detection device 600 in a compact position, in which a telescoping handle 620 is retracted. As illustrated, the blood detection device 600 includes a grip portion 610 configured to allow a user to hold the blood detection device 600. The grip 610 is attached to a telescoping handle 620 that includes multiple sections 630 and 640 configured to retract within one another. According to the illustrated embodiment, secured to the end of the telescoping handle 620 is a head portion 650 configured to detect blood. According to various embodiments, the blood detection device 600 may include an on/off switch 670, a light 680, and/or a speaker 685 to alert an operator that the device is turned on and/or that blood has been detected. According to various embodiments, audio and visual feedback may be provided for a variety of functions, such as when the blood detection device 600 is turned on, has detected blood, has not detected blood, is working correctly, is calibrated, and/or is turned off. Audio alerts may be in the form of prerecorded messages or tones.

As previously described, the blood detection device 600 includes a light source, or transmitter 690, and a receiver 695. The light source 690 may be configured to irradiate a region according to any of the embodiments described herein, including irradiating a region with light at two specific wavelengths. The receiver 695 may be configured to detect and/or determine the intensity of light at two wavelengths. According to one embodiment, the light source 690 comprises transmitter circuitry and LEDs configured to emit light at various wavelengths, at least one of which is generally absorbed by hemoglobin. According to one embodiment, the receiver 695 comprises at least one photodiode, wavelength selective photodiode, voltage controlled wavelength selective photodiode, and/or other light intensity detector. Alternatively, the receiver 695 may comprise at least one broad-spectrum light detector coupled with one or more filters.

As has been previously described, the beam width of the light transmitter 690 and the total area from which the receiver 695 gathers light affect the ability of the blood detection device 600 to detect blood within a region. The accuracy of the system may increase as the area of the region irradiated decreases, since more concentrated light is reflected off the irradiated region. Similarly, the accuracy of the system may improve as the area of the region from which reflected light is received decreases. This is exemplified by examining the extreme limits. If the area irradiated contains only blood, and the area from which reflected light is received contains only light reflected off of blood, the detector would have a high signal to noise ratio. As the ratio of blood to other substances in the region under examination decreases, the accuracy may decrease as well. Consequently, it may be desirable to adjust the beam width of emitted light and/or the area from which reflected light is received. According to one embodiment, a beam adjuster knob 660 is located on the head portion 650 of the blood detection device 600 and provides a mechanism to adjust the transmitted beam width and/or to adjust the area from which light is received. The beam width and area from which light is received may be adjusted (e.g., made wider or narrower) depending on the desired resolution, size of blood drops, amount of blood being left behind, and/or other factors. According to one embodiment, a blood detection device 600 may have one adjustment knob 660 that simultaneously adjusts both the transmitted light beam width 690 and the area from which the receiver 695 receives light. Alternatively, the blood detection device 600 may have two adjustment knobs, one for the transmitter 690 and one for the receiver 695.

According to various embodiments, one or more adjustment knobs similar to the adjustment knob 660 adjusts the beam width and/or area from which light is received by adjusting the position of lenses or mirrors relative to a light source or light detector. Conversely, one or more adjustment knobs may adjust the position of the light source or detector relative to lenses or mirrors.

Figure 7A:
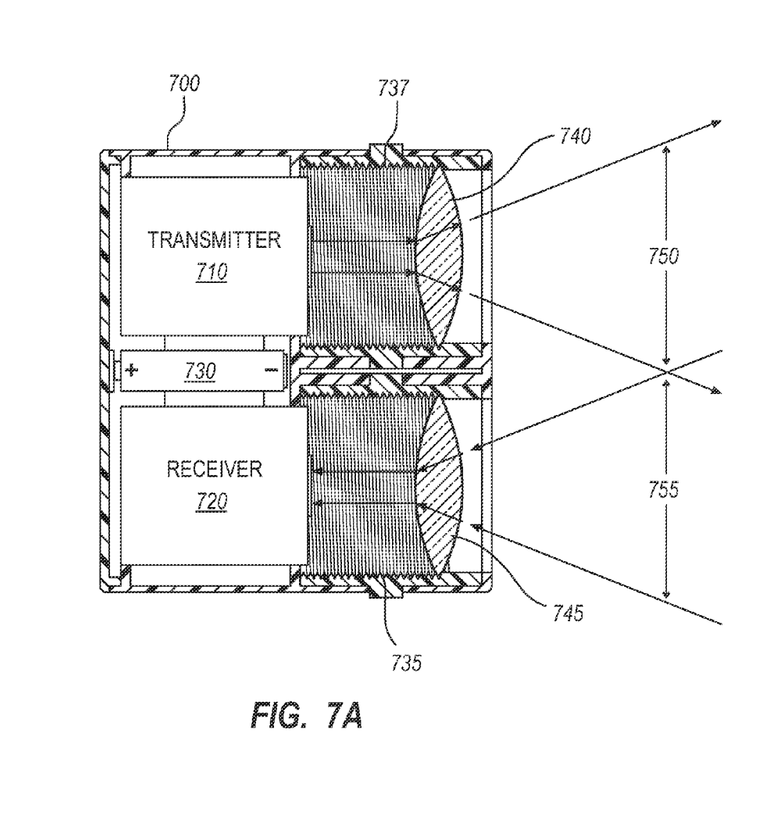
FIGS. 7A and 7B illustrate an exemplary embodiment of a focusing system configured to adjust the beam widths of the transmitter and receiver modules.
Figure 7B:
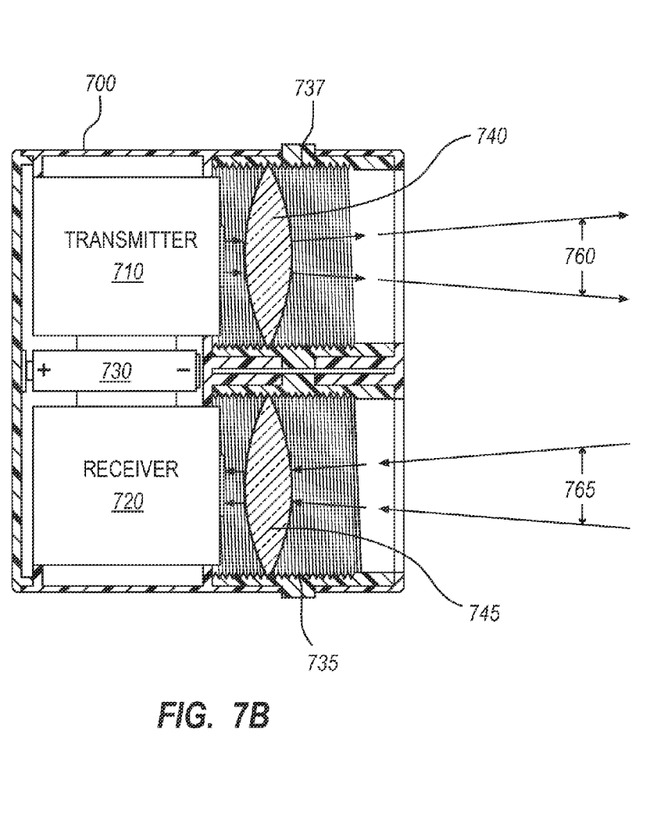

FIGS. 7A and 7B illustrate an exemplary focusing system 700 configured to enable the beam width 750 of the transmitter 710 to be adjusted and the area 755 from which the receiver 720 receives light (herein after referred to as the area 755) to be adjusted. FIG. 7A illustrates the transmitter 710 and receiver 720 with a wide beam width 750 and a wide area 755 respectively. FIG. 7B illustrates a transmitter 710 and a receiver 720 with a narrow beam width 760 and a narrow area 765, respectively.

As illustrated in FIGS. 7A and 7B, the focusing system comprises a transmitter 710 and a receiver 720 configured to transmit and receive light respectively. Lenses 740 and 745 are configured to adjust the beam width 750 and the area 755. As the lenses 740 and 745 are moved toward the transmitter 710 and receiver 720, the beam width 750 and area 755 narrow, as illustrated in FIG. 7B. According to various embodiments, the lenses 740 and 745 are configured to rotate along threads 737 and 735 to adjust their position with respect to transmitter 710 and receiver 720. Also illustrated in FIGS. 7A and 7B is a power source 730 configured to provide power to the focusing system 700 and other components.

According to various alternative embodiments, any of a number of focusing systems may be employed to manually or automatically adjust the beam width 750 and/or area 755, including those that use a lens and/or a mirror. Furthermore, the beam width 750 and the area 755 may be adjusted independently or simultaneously to suit a particular application.

Figure 8:
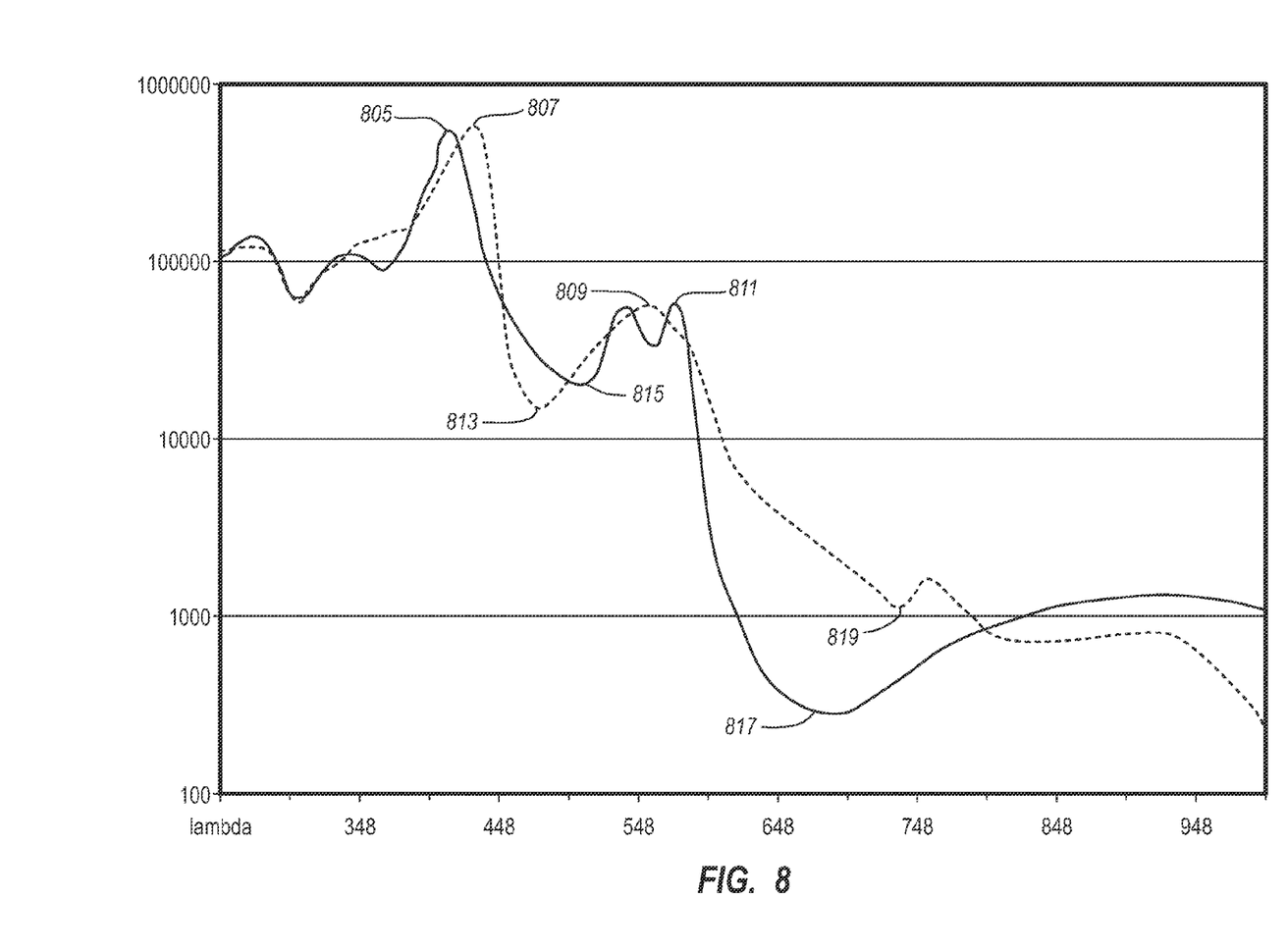
FIG. 8 provides an exemplary graphical depiction of the absorption rates of hemoglobin for particular wavelengths of light.

FIG. 8 illustrates the light absorption of hemoglobin on a logarithmic scale along a spectrum of light wavelengths. Specifically, the solid line represents the absorption of pure hemoglobin (Hb), and the dashed line represents the absorption of hemoglobin and oxygen combined (HbO$_2$). The horizontal axis of the graph represents the wavelength of light and the vertical axis is the molar extinction coefficient. For example, for wavelengths of light less than about 600 nm, the molar extinction coefficient is greater than 10,000, while for wavelengths of light greater than about 600 nm the molar extinction coefficient is approximately 1,000 or less. Thus it can be seen that hemoglobin generally absorbs light with a wavelength less than 600 nm while generally reflecting light with wavelengths greater than 600 nm.

The shape of the graph in FIG. 8 defines the spectral signature for hemoglobin. Typically, substances having well-defined or sharp spectral features, the easier it is to distinguish it from other substances. Thus, features that present strong inflection points may be preferred. As can be seen, there are a number of absorption peaks 805, 807, 809, 811 (areas of high absorption) and valleys 813, 815, 817, 819 (areas of lower absorption). Isobestic points are located at wavelengths where both Hb and HbO$_2$ absorb the same amount of light. According to various embodiments, using isobestic points for a first and second wavelength may be particularly useful. Isobestic points may include 585 nm, 745 nm, and 805 nm.

Wavelengths outside of the visible spectrum may also be used. According to various embodiments, wavelengths are used that correspond to points 805, 807, 809 and/or 811 in FIG. 8. It will be appreciated, however, that the present systems and methods may utilize any number of wavelengths to successfully detect blood in a relatively large region.

The above description provides numerous specific details for a thorough understanding of the embodiments described herein. However, those of skill in the art will recognize that one or more of the specific details may be omitted, or other methods, components, or materials may be used. In some cases, operations are not shown or described in detail.

While specific embodiments and applications of the disclosure have been illustrated and described, it is to be understood that the disclosure is not limited to the precise configuration and components disclosed herein. Various modifications, changes, and variations apparent to those of skill in the art may be made in the arrangement, operation, and details of the methods and systems of the disclosure without departing from the spirit and scope of the disclosure.

What is claimed:

1. A method of detecting blood in a region, comprising:
   receiving light reflected from an irradiated region, including reflected light at a first wavelength and reflected light at a second wavelength;
   determining the intensity of the received reflected light at the first wavelength;
   determining the intensity of the received reflected light at the second wavelength;
   determining that blood is present in the region by subtracting the intensity of the received reflected light at the first wavelength from the intensity of the received reflected light at the second wavelength; and
   wherein the second wavelength is used as a baseline reflection intensity.

2. The method of claim 1, further comprising:
   generating the first wavelength using a first light source;
   generating the second wavelength using a second light source; and
   irradiating the irradiated region using the first light source and the second light source.

3. The method of claim 2, further comprising:
   irradiating the region with a third light source configured to emit light at a third wavelength corresponding to a control wavelength known to be generally reflected by matter other than blood in the region;
   receiving light reflected from the irradiated region at the third wavelength; and
   wherein determining that blood is present in the region is further based on the relative intensity of the received reflected light at the third wavelength.

4. The method of claim 1, wherein the second wavelength corresponds to a control wavelength reflected by matter other than blood in the region.

5. The method of claim 1, wherein the first wavelength is between about 600 nanometers and about 825 nanometers and the second wavelength corresponds to a control wavelength reflected by matter other than blood in the region.

6. The method of claim 1, wherein determining that blood is present in the region is further based on the determining the level of absorption of the reflected light at the first wavelength and the level of absorption of the reflected light at the second wavelength.

7. The method of claim 1, wherein an optical filter is used to isolate specific wavelengths.

8. The method of claim 1, wherein a filter is used to remove ambient light from the reflected light from the irradiated region.

9. The method of claim 1, further comprising determining that hemoglobin is present in the region based on the determining the level of absorption of the reflected light at the first wavelength and the level of absorption of the reflected light at the second wavelength.

10. The device of claim 9, wherein the detection circuitry is configured to account for a plurality of reflective surfaces in the irradiated region.

11. A device for detecting the presence of blood in a region comprising:
a light receiver configured to receive light reflected from an irradiated region, including reflected light at a first wavelength and reflected light at a second wavelength;
the light receiver further configured to determine an intensity of the reflected light at the first wavelength and an intensity of reflected light at the second wavelength;
an analyzer configured to determine that blood is present in the region by subtracting the intensity of the reflected light at the first wavelength from the intensity of the reflected light at the second wavelength received by the light receiver; and
wherein the reflected light at the second wavelength is used as a baseline reflection intensity.

12. The device of claim 11, further comprising:
a first light source configured to generate light at the first wavelength;
a second light source configured to generate light at the second wavelength; and
wherein the first light source and the second light source are used to irradiate the region.

13. The device of claim 12, further comprising:
a third light source configured to emit light at a third wavelength corresponding to a control wavelength generally reflected by matter other than blood in the region;
wherein the receiver is further configured to receive light reflected from the irradiated region at the third wavelength; and
wherein the analyzer is further configured to determine that blood is present in the region based on the relative intensity of the received reflected light at the third wavelength.

14. The device of claim 12, wherein the first light source and the second light source and the light receiver are positioned at the end of a handle.

15. The device of claim 12, wherein the beam width of the first light source and the beam width of the second light source are adjustable to vary the area in the irradiated region that reflects the emitted light.

16. The device of claim 11, wherein the second wavelength of light is a control wavelength reflected by matter other than blood in the region.

17. The device of claim 11, wherein the light receiver is configured with an adjustable focus configured to adjust the area of the region from which reflected light is received by the light receiver.

18. The device of claim 11, wherein the device is configured to be coupled to a global positioning system (GPS) device such that the coordinates of locations where blood has been detected are recorded.

19. The device of claim 18, wherein the coordinates corresponding to locations where blood has been detected are plotted on a map to establish a blood trail.

20. The device of claim 11, further comprising a detection circuitry configured to compensate for the distance between the light receiver and the irradiated region.

21. A portable device for detecting the presence of blood in a region comprising:
a handle comprising a first end and a second end;
a light transmitter attached to the second end of the handle configured to irradiate a region with light at a first wavelength and light at a second wavelength;
a light receiver attached to the second end of the handle configured to receive light reflected from the irradiated region and determine an intensity of reflected light at the first wavelength and an intensity of reflected light at the second wavelength;
an analyzer configured to determine the presence of based, at least in part, on the relative intensities of the received reflected light at the first wavelength and the received reflected light at the second wavelength, by subtracting the intensity of the received reflected light at the first wavelength from the intensity of the received reflected light at the second wavelength, and wherein the second wavelength is used as a baseline reflection intensity; and
a power source configured to provide power to at least the light transmitter, the light receiver, and the analyzer.

22. The portable device of claim 21, wherein the handle comprises a telescoping handle, such that the second end of the handle is configured to extend away from the first end of the handle.

23. The portable device of claim 21, wherein the light transmitter comprises a focusing member configured to adjust the beam width of radiated light to optimize the accuracy of the light receiver based on the region.

24. The portable device of claim 21, wherein the light receiver comprises a focusing member configured to adjust the area of the region from which reflected light is received by the light receiver.

25. The portable device of claim 21, wherein the second wavelength is about 600 nanometers and 825 nanometers.

* * * * *